United States Patent [19]
Fuchs et al.

[11] Patent Number: 5,481,037
[45] Date of Patent: Jan. 2, 1996

[54] DECONTAMINATION OF TERTIARY AMINES FROM PRIMARY AND SECONDARY AMINES

[75] Inventors: Eberhard Fuchs, Frankenthal; Tom Witzel, Ludwigshafen; Klaus P. Stadler, Neustadt, all of Germany

[73] Assignee: BASF Aktiengesellschaft, Ludwigshafen, Germany

[21] Appl. No.: 299,065

[22] Filed: Aug. 31, 1994

[30] Foreign Application Priority Data

Sep. 20, 1993 [DE] Germany ............... 43 31 840.1

[51] Int. Cl.⁶ .................. C07C 209/84; C07C 209/86
[52] U.S. Cl. .................. 564/437; 564/439; 564/462; 564/497; 564/498; 564/499
[58] Field of Search ............... 564/437, 439, 564/497, 498, 499, 462

[56] References Cited

U.S. PATENT DOCUMENTS 3,855,298  12/1974  Bathellier et al. ............... 564/499
4,174,351  11/1979  Shoffner ............... 564/499 X

FOREIGN PATENT DOCUMENTS 3926765  2/1991  Germany.
3942793  5/1991  Germany.
298503   2/1992  Germany.

OTHER PUBLICATIONS

Kampmann et al, Chemical Abstracts, vol. 115 (1991) 135511f.

*Primary Examiner*—Richard L. Raymond
*Attorney, Agent, or Firm*—John H. Shurtleff

[57] ABSTRACT

A process for the purification of tertiary amines in a crude mixture contaminated with undesirable primary and secondary amines which may have only a slight variance in boiling point with respect to the tertiary amine, wherein the crude mixture of the tertiary amine is treated at temperatures which may range from 0° to 200° C. but preferably from 20 to 150° C. and at pressures of from 1 to 200 bar but most preferably under atmospheric pressure with a carboxylate of the formula $$R^4-\overset{\overset{\displaystyle O}{\|}}{C}-O-R^5, \qquad II$$

in which $R^4$ and $R^5$ are selected from the group consisting of $C_1-C_{20}$-alkyl, $C_3-C_{12}$-cycloalkyl, $C_4-C_{20}$-cycloalkylalkyl, and aryl or $C_7-C_{20}$-aralkyl, both optionally mono- to penta-substituted by $C_1-C_8$-alkyl, $C_3-C_8$-cycloalkyl, or $C_4-C_{12}$-cycloalkylalkyl, and $R^4$ may also represent hydrogen, to selectively form the alkylamides of the primary and secondary amine contaminants; and then separating the alkylamides from the tertiary amine by distillation.

15 Claims, No Drawings

DECONTAMINATION OF TERTIARY AMINES FROM PRIMARY AND SECONDARY AMINES

The invention relates to a process to reduce the content of primary and secondary amines in a tertiary amine by treatment with carboxylates.

For manufacturing reasons, small amounts of primary and secondary amines are present in tertiary amines. Purification by distillation is in most cases only possible at great expense, since there is frequently only a very slight variance between the boiling points. However, a content of secondary amine is particularly undesirable due to the danger of the formation of nitrosamines.

To avoid primary or secondary amines, it is recommended in DE-A3,942,793 to add an aldehyde such as formaldehyde or butyraldehyde.

These processes do make it possible to lower the percentage of undesirable amines, but the water produced by the reaction of the NH group with the aldehyde is very difficult to remove by distillation techniques. Moreover, reassociation to primary or secondary amines and aldehyde takes place on heating of the resulting imine or enamine in the presence of the water.

DE-A 3,926,765 (corresponding to CA-A 2,023,057) teaches that it is possible to lower the content of primary or secondary amines by the addition of an organic anhydride. The reaction of the anhydride with the NH group then leads to an amide with the elimination of carboxylic acid. A disadvantage of this process is the liberation of the carboxylic acid, which forms a salt with the tertiary amine and thus leads to losses of yield.

According to DD-A 298,503, isocyanates are used for the removal of primary or secondary amines. However, this process suffers from the drawback that isocyanates are toxic and thus should not be added in superstoichiometric quantities.

It is thus an object of the present invention to overcome the aforementioned drawbacks.

Accordingly, we have found a novel and improved process for the decontamination of tertiary amines of the general formula I

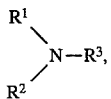
(I)

in which
$R^1$, $R^2$, and $R^3$ denote:

$C_1$–$C_{20}$ alkyl, $C_2$–$C_{20}$ dialkylamino-$C_2$–$C_{10}$ alkyl, $C_1$–$C_{10}$ alkoxy-$C_2$–$C_{10}$ alkyl, $C_2$–$C_{20}$ hydroxyalkyl, $C_3$–$C_{12}$ cycloalkyl, $C_4$–$C_{20}$ cycloalkylalkyl, $C_2$–$C_{20}$ alkenyl, $C_4$–$C_{30}$ dialkylaminoalkenyl, $C_3$–$C_{30}$ alkoxyalkenyl, $C_3$–$C_{20}$ hydroxyalkenyl, $C_5$–$C_{20}$ cyclo-alkylalkenyl, or aryl or $C_7$–$C_{20}$ aralkyl, both optionally mono- to penta-substituted by $C_1$–$C_8$ alkyl, $C_2$–$C_8$ dialkylamino, $C_1$–$C_8$ alkoxy, hydroxy, $C_3$–$C_8$ cycloalkyl, or $C_4$–$C_{12}$ cycloalkylalkyl, from primary and secondary amines, wherein the contaminated mixture containing tertiary amine and primary and secondary amines is treated at temperatures ranging from 0° to 200° C. and pressures of from 1 to 200 bar with carboxylates of the general formula II

in which
$R^4$ and $R^5$ denote $C_1$–$C_{20}$ alkyl, $C_3$–$C_{12}$ cycloalkyl, $C_4$–$C_{20}$ cycloalkylalkyl, or aryl or $C_7$–$C_{20}$ aralkyl, both optionally mono- to penta-substituted by $C_1$–$C_8$ alkyl, $C_3$–$C_8$ cycloalkyl, or $C_4$–$C_{12}$ cycloalkylalky, and $R^4$ further represents hydrogen.

The process of the invention can be carried out as follows:

The contaminated mixture containing tertiary amine I and primary and secondary amines can be treated by the addition of carboxylates II at temperatures ranging from 0° to 200° C. and preferably from 20° to 150° C. and more preferably from 30° to 130° C. and pressures of from 1 to 200 bar and preferably from 1 to 10 bar and more preferably at atmospheric pressure (standard pressure).

The alkylamides of the primary and secondary amines thus formed can be separated by conventional purifying techniques, for example, by distillation. The alcohol $R^5OH$ also liberated during the reaction and excess carboxylate (II) can also be separated by distillation, for example.

Following the reaction of the primary and secondary amines, the tertiary amine can be separated from the reaction mixture by distillation, for example.

Usually, the carboxylate II is added to the primary and secondary amines in a molar ratio of from 5:1 to 1:1 and preferable from 2:1 to 1.1:1.

The amount of primary and secondary amine can be determined, for example, by gas chromatography or by titration of the thio-acids obtained from primary and secondary amines by reaction with carbon disulfide.

Particularly suitable carboxylates II are alkyl carboxylates such as $C_1$–$C_{20}$ alkyl $C_1$–$C_{20}$ alkylcarboxylates and preferably $C_1$–$C_8$ alkyl $C_1$–$C_8$ alkylcarboxylates such as methyl butyrate, ethyl butyrate, methyl propionate, ethyl propionate, methyl acetate, ethyl acetate, methyl formate and ethyl formate and more preferably methyl formate.

The high reactivity of methyl formate allows for the purification proposed in the present invention to be carried out with little or no heating but it can also be carried out at elevated temperatures.

Mixtures of tertiary amine I and primary and secondary amines are generally obtained during preparation of primary amines by reductive alkylation with aldehydes or ketones, in nitrile hydrogenations or in the alkylation of amines with alcohols, for example in the reaction of cyclohexylamine with methanol or the reaction of adipodinitrile with dimethylamine.

The substituents $R^1$, $R^2$, $R^3$, $R^4$, and $R^5$ in the compounds I and II have the following meanings:

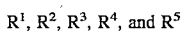

$C_1$–$C_{20}$ alkyl and preferably $C_1$–$C_8$ alkyl and more preferably $C_1$–$C_4$ alkyl such as methyl, ethyl, n-propyl, isopropyl, n-butyl, isobutyl, sec-butyl and tert-butyl, $C_3$–$C_{12}$ cycloalkyl and preferably $C_3$–$C_8$ cycloalkyl and more preferably $C_5$–$C_8$ cycloalkyl such as cyclopentyl and cyclohexyl, $C_4$–$C_{20}$ cycloalkylalkyl and preferably $C_4$–$C_{12}$ cycloalkylalkyl and more preferably $C_4$–$C_8$ cycloalkylalkyl such as cyclohexylmethyl and cyclohexylethyl, aryl such as phenyl, 1-naphthyl, and 2-naphthyl and preferably phenyl, $C_7$–$C_{20}$ aralkyl and preferably $C_7$–$C_{12}$ phenylalkyl and more preferably benzyl, phenylmethyl, and phenylethyl, aryl mono- to penta-substituted by $C_1$–$C_8$ alkyl, $C_2$–$C_8$ dialkylamino, $C_1$–$C_8$ alkoxy, hydroxy, $C_3$–$C_8$ cycloalkyl, or $C_4$–$C_{12}$ cycloalkylalkyl; phenyl mono- to tri-substituted by $C_1$–$C_4$ alkyl, $C_2$–$C_4$ dialkylamino, $C_1$–$C_4$ alkoxy, hydroxy, $C_5$–$C_8$ cycloalkyl, or $C_4$–$C_8$ cycloalkylalkyl; such as methylphenyl, dimethylphenyl and trimethylphenyl, $C_7$–$C_{20}$ aralkyl mono- to penta-substituted by $C_1$–$C_8$ alkyl, $C_2$–$C_8$ dialkylamino, $C_1$–$C_8$ alkoxy, hydroxy, $C_3$–$C_8$ cycloalkyl, or $C_4$–$C_{12}$ cycloalkylalkyl; $C_7$–$C_{20}$ aralkyl mono- to tri-substituted by $C_1$–$C_4$ alkyl, $C_2$–$C_4$ dialkylamino, $C_1$–$C_4$ alkoxy, hydroxy, $C_5$–$C_8$ cycloalkyl, or $C_4$–$C_8$ cycloalkylalkyl; such as 3,4-dimethoxy-phenylethyl, $R^1$, $R^2$, and $R^3$, $C_2$–$C_{20}$ dialkylamino-$C_2$–$C_{10}$ alkyl and preferably $C_2$–$C_{10}$ dialkylamino-$C_2$–$C_7$ alkyl such as dimethylaminoethyl, dimethylaminopropyl, dimethylaminobutyl, dimethylaminopentyl, dimethylaminohexyl, dimethylaminoheptyl, diethylaminoethyl, diethylaminopropyl, diethylaminobutyl, diethylaminopentyl, diethylaminohexyl, diethylaminoheptyl, dipropylaminoethyl, dipropylaminopropyl, dipropylaminobutyl, dipropylaminopentyl, dipropylaminohexyl, dipropylaminoheptyl;

$C_1$–$C_{10}$ alkoxy-$C_2$–$C_{10}$ alkyl and preferable $C_1$–$C_6$ alkoxy, $C_2$–$C_5$ alkyl such as methoxyethyl, methoxypropyl, ethoxyethyl, ethoxypropyl, propoxyethyl and propoxypropyl, $C_2$–$C_{20}$ hydroxyalkyl and preferably $C_1$–$C_8$ hydroxyalkyl and more preferably $C_1$–$C_4$ hydroxyalkyl such as hydroxymethyl, 2-hydroxyethyl, 2-hydroxypropyl, 3-hydroxypropyl, $C_2$–$C_{20}$ alkenyl and preferably $C_2$–$C_8$ alkenyl and more preferably $C_2$–$C_4$ alkenyl such as vinyl and allyl.

$C_4$–$C_{30}$ dialkylaminoalkenyl and preferably $C_4$–$C_{16}$ dialkylaminoalkenyl and more preferably $C_4$–$C_{12}$ dialkylaminoalkenyl, $C_3$–$C_{30}$ alkoxyalkenyl and preferably $C_3$–$C_{16}$ alkoxyalkenyl and more preferably $C_3$–$C_{12}$ alkoxyalkenyl, $C_3$–$C_{20}$ hydroxyalkenyl and preferably $C_2$–$C_8$ hydroxyalkenyl and more preferably $C_2$–$C_8$ hydroxyalkenyl, $C_5$–$C_{20}$ cycloalkylalkenyl and preferably $C_5$–$C_{12}$ cycloalkylalkenyl and more preferably $C_5$–$C_{12}$ cycloalkylalkenyl, $R^4$, hydrogen.

The tertiary amines I are suitable as solvents, extracting agents, catalysts for polyurethane foams free from fluorochlorocarbons, catalysts for epoxy resins, corrosion inhibitors, intermediates for bactericides, herbicides and pharmaceuticals (Kirk-Othmer, *Encyclopedia of Chemical Technology*, Vol. 2, 1978. 3rd Edition, J. Wiley and Sons, New York, p. 279 et seq).

EXAMPLES

Example 1

To a mixture of 95% of dimethylcyclohexylamine, 2.5% of methylcyclohexylamine, and 2.5% of cyclohexylamine there is added, per mole of NH function, 1.1 tool of methyl formate, after which the mixture is heated at the boil for 2 h. Following distillation, dimethylcyclohexylamine having a purity above 99.5% can be obtained in a yield of more than 97%.

Example 2

To a crude mixture of tetramethylhexamethylenediamine, which is contaminated with various primary and secondary amines, there are added, per mole of NH function, 1.1 mol of methyl formate, and the mixture is heated at 90° C. for 2 h. Following distillation, the tetramethylhexamethylenediamine can be obtained in a form which is free from primary and secondary amines.

We claim:

1. A process for the purification of tertiary amines contaminated with undesirable primary and secondary amines, which comprises:

treating a crude mixture of the tertiary amine containing said primary and secondary amines at temperatures ranging from 0° to 200° C. and pressures of from 1 to 200 bar with a carboxylate of the formula $$R^4-\overset{O}{\underset{\|}{C}}-O-R^5, \qquad II$$

in which $R^4$ and $R^5$ are selected from the group consisting of $C_1$–$C_{20}$-alkyl, $C_3$–$C_{12}$-cycloalkyl, $C_4$–$C_{20}$-cycloalkylalkyl, and aryl or $C_7$–$C_{20}$-aralkyl, both optionally mono- to penta-substituted by $C_1$–$C_8$-alkyl, $C_3$–$C_8$-cycloalkyl, or $C_4$–$C_{12}$-cycloalkylalkyl, and $R^4$ also represent hydrogen, to selectively form the alkylamides of the primary and secondary amine contaminants; and separating the alkylamides from the tertiary amine by distillation.

2. A process as claimed in claim 1, wherein the tertiary amine to be purified has the formula $$\begin{matrix} R^1 \\ \phantom{R}\diagdown \\ \phantom{RR}N-R^3, \\ \phantom{R}\diagup \\ R^2 \end{matrix} \qquad I$$

in which $R^1$ $R^2$ and $R^3$ are selected from the group consisting of $C_1$–$C_{20}$-alkyl, $C_2$–$C_{20}$-dialkylamino-$C_2$–$C_{10}$-alkyl, $C_1$–$C_{10}$-alkoxy-$C_2$–$C_{10}$-alkyl, $C_2$–$C_{20}$-hydroxyalkyl, $C_3$–$C_{12}$-cycloalkyl, $C_4$–$C_{20}$-cycloalkylalkyl, $C_2$–$C_{20}$-alkenyl, $C_4$–$C_{30}$-dialkylaminoalkenyl, $C_3$–$C_{30}$-alkoxyalkenyl, $C_3$–$C_{30}$-hydroxyalkenyl, $C_5$–$C_{20}$-cycloalkylalkenyl, and aryl or $C_7$–$C_{20}$-aralkyl, both optionally mono- to pentasubstituted by $C_1$–$C_8$-alkyl, $C_2$–$C_8$-dialkylamino, $C_1$–$C_8$-alkoxy, hydroxy, $C_3$–$C_8$-cycloalkyl, or $C_4$–$C_{12}$ cycloalkylalkyl.

3. A process as claimed in claim 1, wherein the carboxylate of the formula II is one in which $R^4$ denotes hydrogen and $R^5$ denotes $C_1$–$C_8$-alkyl.

4. A process as claimed in claim 1, wherein methyl formate is used as carboxylate II.

5. A process as claimed in claim 1, wherein the treatment is carried out at temperatures ranging from 20° to 150° C.

6. A process as claimed in claim 1, wherein the treatment is carried out at atmospheric pressure.

7. A process as claimed in claim 1, wherein the molar ratio of carboxylate II to primary and secondary amines is from 5:1 to 1:1 einsetzt.

8. A process as claimed in claim 1, wherein the molar ratio of carboxylate II to primary and secondary amines is from 2:1 to 1.1:1 einsetzt.

9. A process as claimed in claim 1, wherein the tertiary amine of the formula I is one in which each of $R^1$, $R^2$ and $R^3$ denotes $C_1$–$C_4$-alkyl.

10. A process as claimed in claim 1, wherein said crude mixture is treated at temperatures ranging from 20° to 150° C. and pressures of from 1 to 10 bar with said carboxylate II.

11. A process as claimed in claim 10, wherein said crude mixture is treated at atmospheric pressure.

12. A process as claimed in claim 1, wherein said crude mixture is treated at temperatures ranging from 30° to 130° C. and pressures of from 1 to 10 bar with said carboxylate II.

13. A process as claimed in claim 9, wherein said crude mixture is treated at temperatures ranging from 20° to 150° C. and pressures of from 1 to 10 bar with said carboxylate II.

14. A process as claimed in claim 13, wherein said crude mixture is treated at atmospheric pressure.

15. A process as claimed in claim 1 wherein the carboxylate II is methyl formate.

* * * * *

UNITED STATES PATENT AND TRADEMARK OFFICE
CERTIFICATE OF CORRECTION

PATENT NO. : 5,481,037

DATED : January 2, 1996

INVENTOR(S) : Fuchs et al.

It is certified that error appears in the above-identified patent and that said Letters Patent is hereby corrected as shown below:

Column 4, line 61 and 64:

Claim 7 and 8, line 3 of each, cancel the German word "einsetzt".

Signed and Sealed this

Second Day of April, 1996

*Attest:*

BRUCE LEHMAN

*Attesting Officer*      *Commissioner of Patents and Trademarks*